United States Patent [19]

Inomata et al.

[11] Patent Number: 5,196,558
[45] Date of Patent: Mar. 23, 1993

[54] SILOXANE COMPOUNDS

[75] Inventors: Hiroshi Inomata, Annaka; Yasushi Yamamoto; Yasuo Tarumi, both of Takasaki; Kenichi Fukuda, Annaka, all of Japan

[73] Assignee: Shin-Etsu Chemical Company, Limited, Tokyo, Japan

[21] Appl. No.: 925,147

[22] Filed: Aug. 6, 1992

[30] Foreign Application Priority Data

Aug. 7, 1991 [JP] Japan .................. 3-222131
Aug. 15, 1991 [JP] Japan .................. 3-229428

[51] Int. Cl.$^5$ .............................. C07F 7/08
[52] U.S. Cl. .................... 556/434; 556/445; 549/215
[58] Field of Search ............... 549/215; 556/434, 445

[56] References Cited

U.S. PATENT DOCUMENTS

| | | | |
|---|---|---|---|
| 3,542,830 | 11/1970 | Kein et al. | 556/434 X |
| 3,627,801 | 12/1971 | Pierce et al. | 556/434 X |
| 3,647,740 | 3/1972 | Loree et al. | 556/434 X |
| 3,818,064 | 6/1974 | Kim | 556/434 X |
| 4,057,566 | 11/1977 | Carter et al. | 556/434 |

FOREIGN PATENT DOCUMENTS 62-47605 3/1987 Japan .
62-47608 3/1987 Japan .
62-49305 3/1987 Japan .

OTHER PUBLICATIONS

English Language Abstract of Japan 62-47605.
English Language Abstract of Japan 62-47608.
English Language Abstract of Japan 62-49305.

*Primary Examiner*—Paul F. Shaver
*Attorney, Agent, or Firm*—Millen, White, Zelano and Branigan

[57] ABSTRACT

Novel siloxane compounds are provided which have 1-5 hydrogen atoms each attached to a silicon atom (SiH group) and 1-5 epoxy or alkoxy - containing organic groups each attached to a silicon atom in a molecule. These siloxane compounds are useful tackifiers to conventional resins, have good affinity to fluorinated silicone resins and rubbers so that they impart adhesion to fluorinated silicone resins and rubbers, and contribute to solvent resistance and minimal moisture permeability.

8 Claims, 6 Drawing Sheets

SILOXANE COMPOUNDS

This invention relates to novel siloxane compounds, and more particularly, to siloxane compounds effective for imparting adhesion to silicone resins and the like in bonding them to various supports.

BACKGROUND OF THE INVENTION

It was a common practice in the prior art to blend siloxane compounds in silicone resins for imparting adhesion to the silicone resins. For example, Japanese Patent Application Kokai Nos. 47605/1987, 47608/1987 and 49305/1987 disclose hydrogensiloxanes having a perfluoropolyether group or perfluoroalkylene group in a backbone and at least two SiH groups in a molecule. They are of the following formula (5).

(5)

In the formula, Rf is a perfluoropolyether group or perfluoroalkylene group and p is equal to 1, 2 or 3. These siloxane compounds are, however, difficult to impart sufficient adhesion to fluorinated silicone resins. There is a need for the development of siloxane compounds capable of imparting sufficient adhesion to fluorinated silicone resins too.

SUMMARY OF THE INVENTION

An object of the present invention is to provide a novel siloxane compound which has good affinity to fluorinated silicone resins and rubbers and greatly contributes to solvent resistance and has minimal moisture permeability.

The inventors have found that novel siloxane compounds of the following general formula (1) are obtained by effecting an addition reaction of 1 to 5 equivalents of epoxy or alkoxy compounds having an aliphatic double bond to hydrogensiloxanes of the following general formula (6).

(1)

In formula (1), Rf is a perfluoropolyether group or perfluoroalkylene group, X is a group of the following formula (2), (3) or (4), and letters n and m are integers of from 0 to 3 meeting $0 < n+m \leq 5$.

(2)

(3)

(4)

In formulae (2) and (3), $R^1$ is a divalent organic group, $R^2$ is a monovalent hydrocarbon group, and k is an integer of from 0 to 2.

(6)

In formula (6), Rf is as defined above.

According to our finding, since the siloxane compounds of formula (1) have in a molecule at least one hydrogen atom attached to a silicon atom reactive with silicone resins (SiH group) and at least one organic group containing an epoxy or alkoxy group attached to a silicon atom participating in adhesion to substrates or adherents, these siloxane compounds have good affinity to fluorinated silicone resins and rubbers and greatly contribute to solvent resistance and minimal moisture permeability. The siloxane compounds of formula (1) are thus useful tackifiers capable of imparting adhesion to fluorinated silicone resins and rubbers.

DETAILED DESCRIPTION OF THE INVENTION

The siloxane compounds of the present invention are of the general formula (1).

(1)

In formula (1), Rf is a perfluoropolyether group or perfluoroalkylene group. Preferably, the perfluoropolyether groups have 4 to 15 carbon atoms and are typically represented by the following formulae (7) and (8).

(7)

Y is F or $CF_3$, and letters x and y are equal to 0, 1 or 2, meeting $0 \leq x+y \leq 3$.

(8)

Y, x and y are as defined above, and z is an arbitrary integer, preferably from 1 to 6.

Examples of the perfluoropolyether group are given below.

,

,

-continued

The perfluoroalkylene groups preferably have 2 to 10 carbon atoms and typically are represented by the following formula:

(9)

wherein w is an integer of 2 to 10. Examples include $-C_2F_4-$, $-C_4F_8-$, $-C_6F_{12}-$, and $-C_8F_{16}-$.

In formula (1), X is a group of formula (2), (3) or (4).

In formula (2), $R^1$ is a divalent organic group, preferably a lower alkylene group having 1 to 5 carbon atoms which may have a terminal or intervening oxygen atom. Examples are $-(CH_2)_4-$, $-(CH_2)_2OCH_2-$, $-CH_2CH_2-$, $-(CH_2)_3O-$, and $-(CH_2)_3OCH_2-$.

In formula (4), $R^2$ is a monovalent hydrocarbon group and k is an integer of from 0 to 2. The hydrocarbon groups represented by $R^2$ preferably have 1 to 6 carbon atoms and examples include $C_1$-$C_6$ alkyl groups such as methyl, ethyl and propyl groups, $C_2$-$C_6$ alkenyl groups such as vinyl, isopropenyl and butenyl groups, and cyclohexyl and phenyl groups.

In formula (1), letters n and m are integers of from 0 to 3 meeting $0 < n+m \leq 5$. This implies that the siloxane compounds of formula (1) have in a molecule 1 to 5 hydrogen atoms each attached to a silicon atom (or 1 to 5 SiH groups) and 1 to 5 organic groups containing an epoxy or alkoxy group each attached to a silicon atom.

The siloxane compounds of the present invention can be synthesized by effecting an addition reaction between an organohydrogen-siloxane and an aliphatic double bond-containing epoxy or alkoxy compound, that is, between a SiH bond in the former and an aliphatic double bond in the latter in the presence of a platinum series catalyst. One of the starting reactants is a hydrogensiloxane which is preferably of the general formula:

wherein Rf is a perfluoropolyether group or perfluoroalkylene group.

Preferred examples of the aliphatic double bond-containing epoxy compound are given by the following formulae (10) to (12).

Preferred examples of the aliphatic double bond-containing alkoxy compound are given by the following formula (13)

The addition reaction between the hydrogensiloxane of formula (6) and the aliphatic double bond-containing epoxy or alkoxy compound of formula (10) to (13) may be carried out in a conventional manner using well-known addition reaction catalyst, typically platinum series catalysts. Exemplary catalysts include chloroplatinic acid, olefin complexes of chloroplatinic acid, alcohol-modified complexes of chloroplatinic acid, and vinylsiloxane complexes of chloroplatinic acid. For addition reaction, the temperature is generally 50° to 100° C., preferably 70° to 85° C.

Although the addition reaction may be carried out without solvent, the use of a solvent is preferred for reaction temperature control. Any solvent which does not give rise to side reaction with SiH and epoxy groups or adversely affect the catalyst may be used although those solvents which permit addition reaction under atmospheric pressure are preferred, for example, aromatic hydrocarbons such as benzene, toluene and xylene, and fluorinated aromatic compounds such as benzotrifluoride and m-xylenehexafluoride. At the end of addition reaction, the reaction product may be purified by removing the catalyst through absorption by activated carbon or the like and distilling off the solvent.

EXAMPLE

Examples of the present invention are given below by way of illustration and not by way of limitation.

Example 1

A 200-ml flask equipped with a condenser and thermometer was charged with 30 grams (0.025 mol) of a hydrogensiloxane of formula (14) and 15 grams of toluene and heated to a temperature of 75° to 80° C. With thorough stirring, 1.0 gram of a toluene solution containing 0.024 grams of 2-ethylhexanol-modified platinum catalyst having a platinum concentration of 2% (Pt: $2.5 \times 10^{-6}$ mol) was added dropwise to the flask, and thereafter, 7.9 grams of a toluene solution containing 2.9 grams (0.025 mol) of an epoxy compound of formula (10) was added dropwise over 90 minutes.

(14)

(10)

The reaction mixture was allowed to cool down, shaken for 1 hour together with activated carbon, removed of the activated carbon by filtration, and subjected to vacuum distillation at 80° C. and 10 mmHg for 2 hours for toluene removal, obtaining 35 grams of a product. The product was analyzed by gel permeation chromatography (GPC) to find that it contained 19 grams of a mono-adduct (yield 57%).

The mono-adduct isolated and collected by GPC was analyzed by proton-NMR, mass spectro-scopy, IR absorption spectroscopy, elemental analysis and Si-H content measurement. As a result of these analyses, it was identified to have the structure of formula (15).

(15)

(HSiO)$_3$SiCH$_2$CH$_2$CFOCF$_2$CFOCF$_2$CF$_2$OCFCF$_2$OCFCH$_2$CH$_2$—
 |             |       |       |       |
CH$_3$               CF$_3$     CF$_3$     CF$_3$     CF$_3$           CH$_3$     CH$_3$           O
            |           |           / \
—Si(OSiH)$_2$(OSiCH$_2$CH$_2$CH$_2$OCH$_2$CHCH$_2$)
            |           |
          CH$_3$     CH$_3$

| Elemental analysis | | | | |
|---|---|---|---|---|
| | C | H | Si | F |
| Calcd.* (%) | 30.44 | 4.51 | 16.75 | 33.99 |
| Found (%) | 30.21 | 4.72 | 16.34 | 34.15 |

*calculated as C$_{34}$H$_{60}$O$_{12}$F$_{24}$Si$_8$

Mass spectrometry 1340 (M+)

IR absorption spectrum

Figure 1:
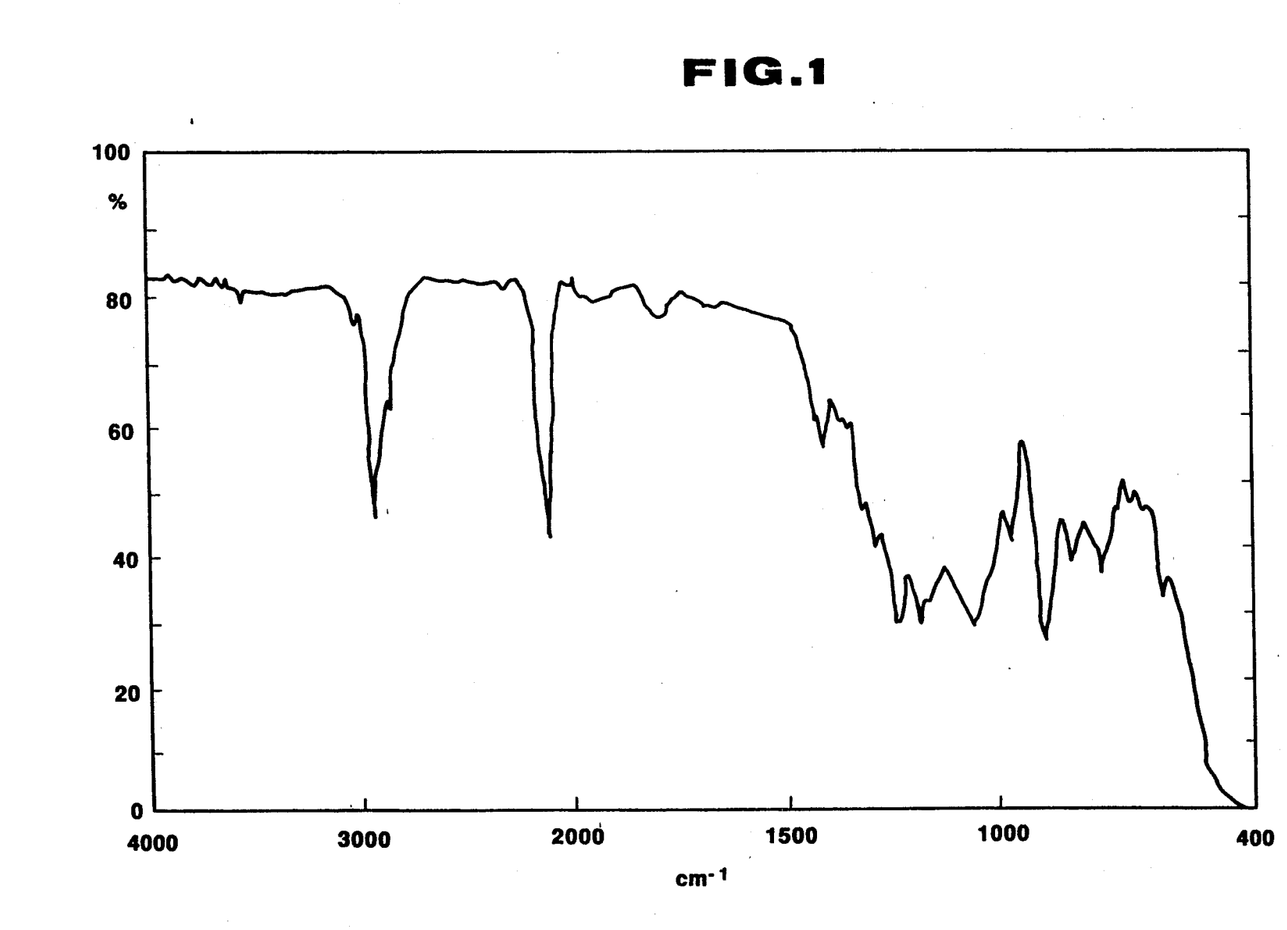
FIGS. 1, 2, 3, 4, 5 and 6 are charts showing the IR absorption spectra of the siloxane compounds obtained in Examples 1, 2, 3, 4, 5, and 7, respectively.

There appeared a characteristic absorption peak attributable to a SiH group at wavenumber 2140 cm$^{-1}$ and a characteristic absorption peak attributable to an epoxy group (C-H) at wavenumber 3000–3080 cm$^{-1}$. FIG. 1 is an IR absorption spectrum chart of the compound.

SiH content

Calcd.: 0.0037 mol/g
Found: 0.0035 mol/g

| $^1$H-NMR spectrum | |
|---|---|
| 4.63~5.04 ppm | (Si—H, m, 5H) |

| $^1$H-NMR spectrum | |
|---|---|
| 0.13~0.57 ppm | (Si—CH$_3$, m, 36H) |
| 0.63~1.10 ppm | (Si—CH$_2$—, m, 6H) |
| 1.70~2.37 ppm | (C—CH$_2$—CF, m, 4H) |
| 1.23~1.70 ppm | (C—CH$_2$—C, m, 2H) |
| 3.40~4.03 ppm | (C—CH$_2$—O, m, 4H) |

| 2.97~3.33 ppm | (—CH——C, m, 1H) with epoxide O |
|---|---|
| 2.47~2.90 ppm | (C——CH$_2$, m, 2H) with epoxide O |

Example 2

A reactor as used in Example 1 was charged with 20 grams (0.019 mol) of a hydrogensiloxane of formula (16) and 10 grams of toluene. In a similar manner as in Example 1, 1.0 gram of a toluene solution containing 0.019 grams of platinum catalyst (Pt: $1.9 \times 10^{-6}$ mol) was added dropwise to the reactor, and thereafter, 7.2 grams of a toluene solution containing 2.2 grams (0.019 mol) of an epoxy compound of formula (10) was added dropwise over 50 minutes.

(16)

(10)

CH$_2$=CHCH$_2$OCH$_2$CH——CH$_2$ (with epoxide O)

By following the same procedure as in Example 1, there was obtained 17.9 grams of a product. The product was analyzed by GPC to find that it contained 8.1 grams of a mono-adduct (yield 36%). As a result of various analyses, the mono-adduct isolated and collected by GPC was identified to have the structure of formula (17).

(17)

| Elemental analysis | | | | |
|---|---|---|---|---|
| | C | H | Si | F |
| Calcd.* (%) | 31.68 | 5.14 | 19.11 | 29.09 | mol) of an epoxy compound of formula (10) was added dropwise over 90 minutes.

| Elemental analysis | | | |
|---|---|---|---|
| C | H | Si | F |
| Found (%) 31.32 | 5.41 | 18.46 | 29.66 |

Mass spectrometry

By following the same procedure as in Example 1, there was obtained 23.4 grams of a product. The product was analyzed by GPC to find that it contained 7.3 grams of a tri-adduct (yield 29%). As a result of various analyses, the tri-adduct isolated and collected by GPC was identified to have the structure of formula (19).

1174 (M+)

IR absorption spectrum

Figure 2:
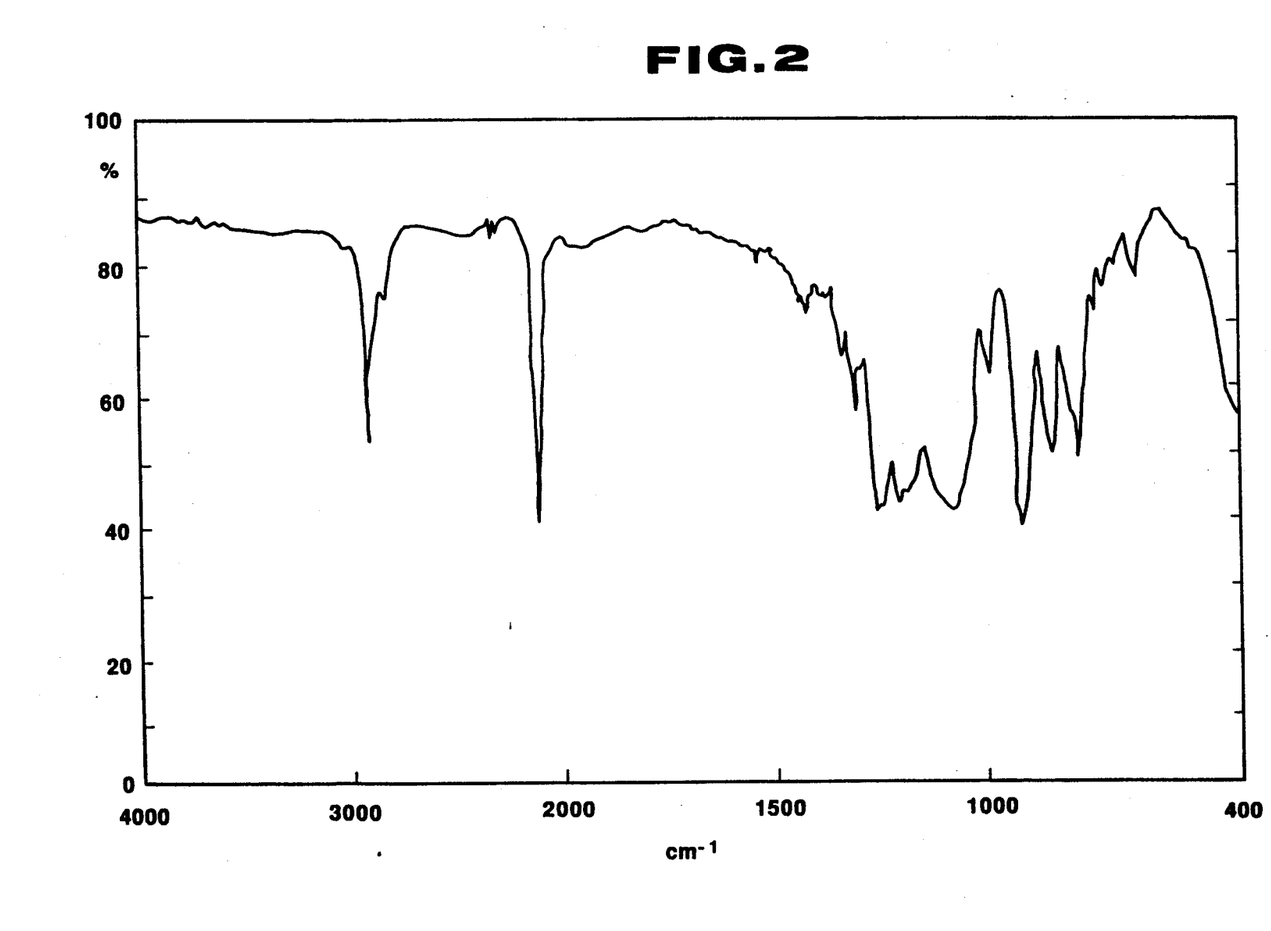

There appeared a characteristic absorption peak attributable to a SiH group at wavenumber 2140 cm$^{-1}$ and a characteristic absorption peak attributable to an epoxy group (C—H) at wavenumber 3000–3080 cm$^{-1}$. FIG. 2 is an IR absorption spectrum chart of the compound.

In the formula, p and q are integers meeting p+q=3.

| | Elemental analysis | | | |
|---|---|---|---|---|
| | C | H | Si | F |
| Calcd.* (%) | 35.20 | 5.14 | 14.29 | 29.05 |
| Found (%) | 34.98 | 5.21 | 14.73 | 28.47 |

*calculated as $C_{48}H_{80}O_{16}F_{24}Si_8$

SiH content

Calcd.: 0.0043 mol/g
Found: 0.0046 mol/g

Mass spectrometry

1568 (M+)

IR absorption spectrum

Figure 3:
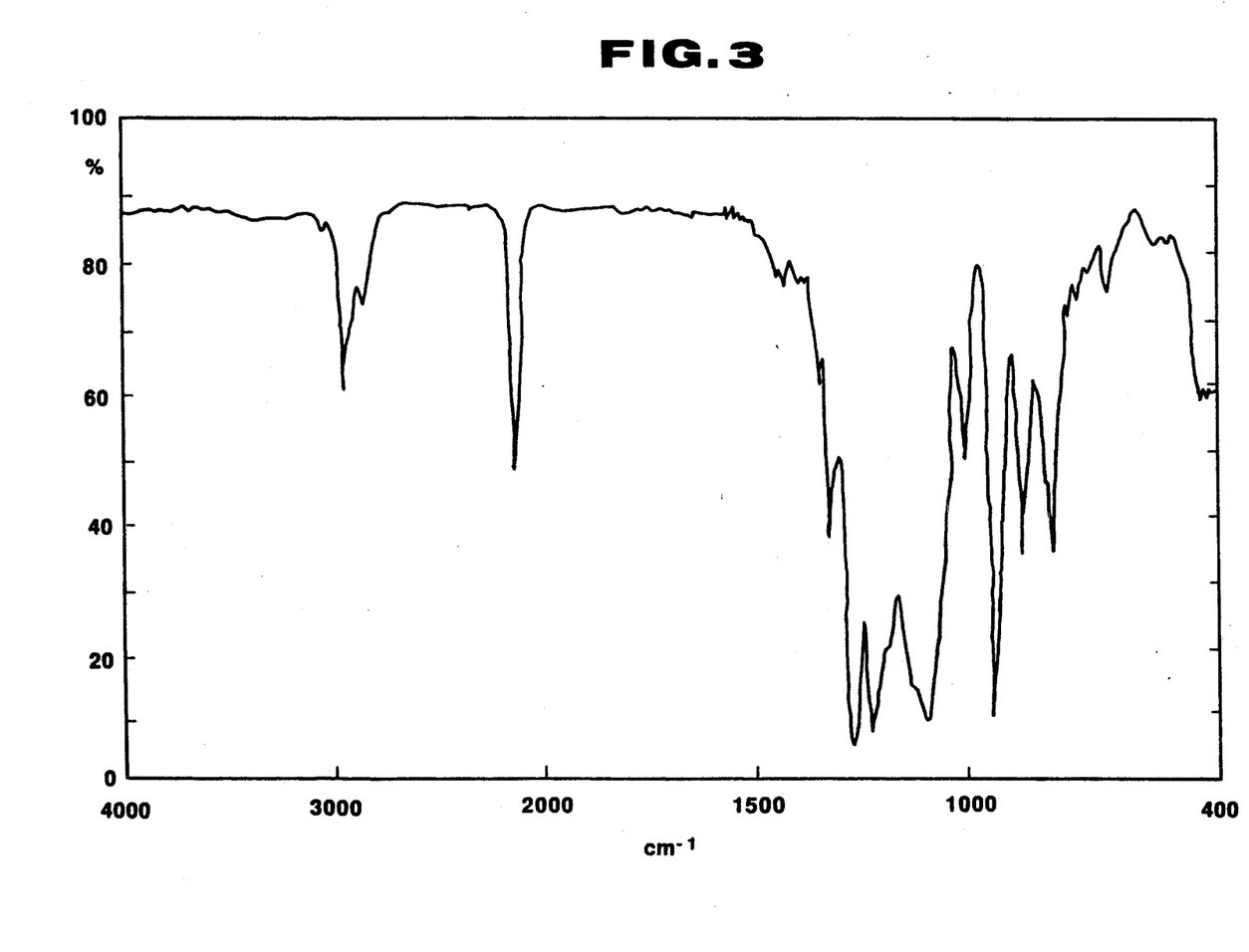

There appeared a characteristic absorption peak attributable to a SiH group at wavenumber 2140 cm$^{-1}$ and a characteristic absorption peak attributable to an epoxy group (C—H) at wavenumber 3000–3080 cm$^{-1}$. FIG. 3 is an IR absorption spectrum chart of the compound.

SiH content

Calcd.: 0.0019 mol/g
Found: 0.0021 mol/g

| $^1$H-NMR spectrum | |
|---|---|
| 4.50~4.83 ppm | (Si—H, m, 5H) |
| 0.03~0.40 ppm | (Si—CH$_3$, m, 36H) |
| 0.67~0.93 ppm | (Si—CH$_2$—, m, 6H) |
| 1.83~2.50 ppm | (C—CH$_2$—CF, m, 4H) |
| 1.40~1.77 ppm | (C—CH$_2$—C, m, 2H) |
| 3.17~3.70 ppm | (C—CH$_2$—O, m, 4H) |
| 2.73~3.13 ppm |  (—CH——C, m, 1H) |
| 2.23~2.77 ppm |  (C——CH$_2$, m, 2H) |

Example 3

A reactor as used in Example 1 was charged with 20 grams (0.016 mol) of a hydrogensiloxane of formula (18) and 10 grams of toluene. In a similar manner as in Example 1, 1.0 gram of a toluene solution containing 0.016 grams of platinum catalyst (Pt: 1.6×10$^{-6}$ mol) was added dropwise to the reactor, and thereafter, 20.5 grams of a toluene solution containing 5.5 grams (0.048

| $^1$H-NMR spectrum | |
|---|---|
| 4.50~4.90 ppm | (Si—H, m, 3H) |
| 0.03~0.37 ppm | (Si—CH$_3$, m, 36H) |
| 0.37~0.90 ppm | (Si—CH$_2$—, m, 10H) |
| 1.77~2.47 ppm | (C—CH$_2$—CF, m, 4H) |
| 1.27~1.77 ppm | (C—CH$_2$—C, m, 6H) |
| 3.13~3.73 ppm | (C—CH$_2$—O, m, 12H) |
| 2.73~3.13 ppm |  (CH——C, m, 3H) |

-continued

| $^1$H-NMR spectrum | |
|---|---|
| 2.23~2.73 ppm |  (C——CH$_2$, m, 6H) |

Example 4

A reactor as used in Example 1 was charged with 20 grams (0.016 mol) of hydrogensiloxane of formula (18) and 10 grams of toluene. In a similar manner as in Example 1, 1.0 gram of a toluene solution containing 0.016 grams of platinum catalyst (Pt: 1.6×10$^{-6}$ mol) was added dropwise to the reactor, and thereafter, 6.6 grams of a toluene solution containing 1.6 grams (0.016 mol) of an epoxy compound of formula (11) was added dropwise over 30 minutes.

(18)

(11)

By following the same procedure as in Example 1, there was obtained 21.0 grams of a product. The product was analyzed by GPC to find that it contained 7.4 grams of a mono-adduct (yield 35%). As a result of various analyses, the mono-adduct isolated and collected by GPC was identified to have the structure of formula (19).

(19)

$$\text{(HSiO)}_3\text{SiCH}_2\text{CH}_2\text{CFOCF}_2\text{CF}_2\text{OCF}_2\text{CF}_2\text{OCFCF}_2\text{OCFCH}_2\text{CH}_2-$$
with CH$_3$, CF$_3$, CF$_3$, CF$_3$, CF$_3$ substituents $$-\text{Si(OSiH)}_2(\text{OSiCH}_2\text{CH}_2\text{CH}_2\text{CH}_2\text{CH}\overset{O}{\frown}\text{CH}_2)$$
with CH$_3$, CH$_3$, CH$_3$, CH$_3$ substituents

| | Elemental analysis | | | |
|---|---|---|---|---|
| | C | H | Si | F |
| Calcd.* (%) | 30.81 | 4.56 | 16.95 | 34.40 |
| Found (%) | 30.60 | 4.91 | 16.37 | 34.79 |

*calculated as C$_{34}$H$_{60}$O$_{11}$F$_{24}$Si$_8$

Mass spectrometry

1324 (M$^+$)

IR absorption spectrum

Figure 4:
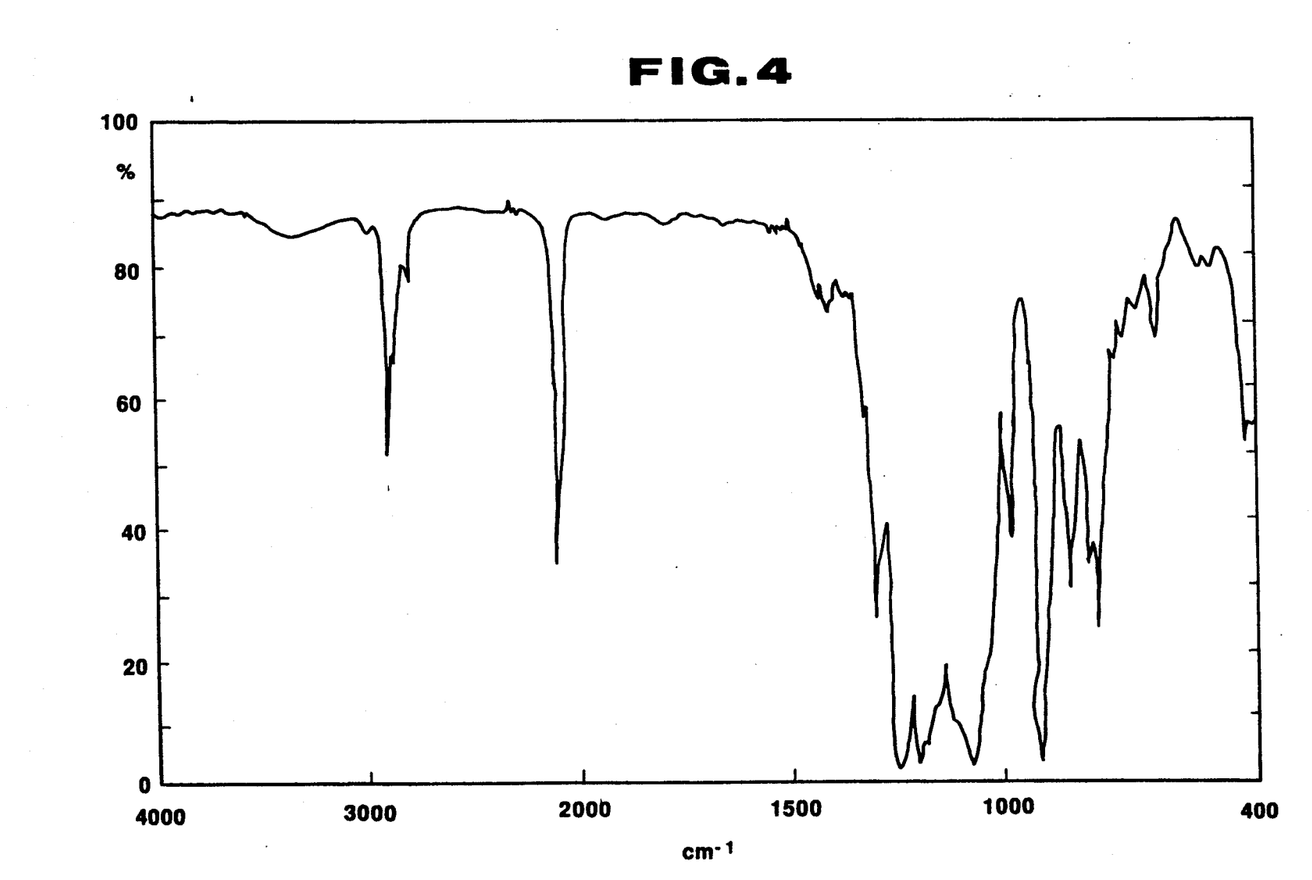

There appeared a characteristic absorption peak attributable to a SiH group at wavenumber 2140 cm$^-$. FIG. 4 is an IR absorption spectrum chart of the compound.

SiH content

Calcd.: 0.0038 mol/g
Found: 0.0033 mol/g

| $^1$H-NMR spectrum | |
|---|---|
| 4.47~4.87 ppm | (Si—H, m, 5H) |
| 0.03~0.37 ppm | (Si—CH$_3$, m, 36H) |
| 0.37~0.97 ppm | (Si—CH$_2$—C, m, 6H) |
| 1.03~1.73 ppm | (C—CH$_2$—C, m, 6H) |
| 1.80~2.50 ppm | (C—CH$_2$—CF, m, 4H) |
| 2.80~3.00 ppm |  (—CH——C, m, 1H) |
| 2.50~2.73 ppm |  (C——CH$_2$, m, 2H) |

Example 5

A reactor as used in Example 1 was charged with 10 grams (0.012 mol) of a hydrogensiloxane of formula (20) and 5 grams of toluene. In a similar manner as in Example 1, 1.0 gram of a toluene solution containing 0.012 grams of platinum catalyst (Pt: 1.2×10$^{-6}$ mol) was added dropwise to the reactor, and thereafter, 4.3 grams of a toluene solution containing 1.3 grams (0.012 mol) of an epoxy compound of formula (10) was added dropwise over 30 minutes.

(20)

(10)

By following the same procedure as in Example 1, there was obtained 11.2 grams of a product. The product was analyzed by GPC to find that it contained 5.5 grams of a mono-adduct (yield 50%). As a result of various analyses, the mono-adduct isolated and collected by GPC was identified to have the structure of formula (21).

(21)

| | Elemental analysis | | | |
|---|---|---|---|---|
| | C | H | Si | F |
| Calcd.* (%) | 34.41 | 6.19 | 22.99 | 23.32 |

-continued

| | Elemental analysis | | | |
|---|---|---|---|---|
| | C | H | Si | F |
| Found (%) | 34.73 | 5.82 | 22.19 | 23.68 |

*calculated as $C_{28}H_{60}O_8F_{12}Si_8$

Mass spectrometry

976 (M+)

IR absorption spectrum

Figure 5:
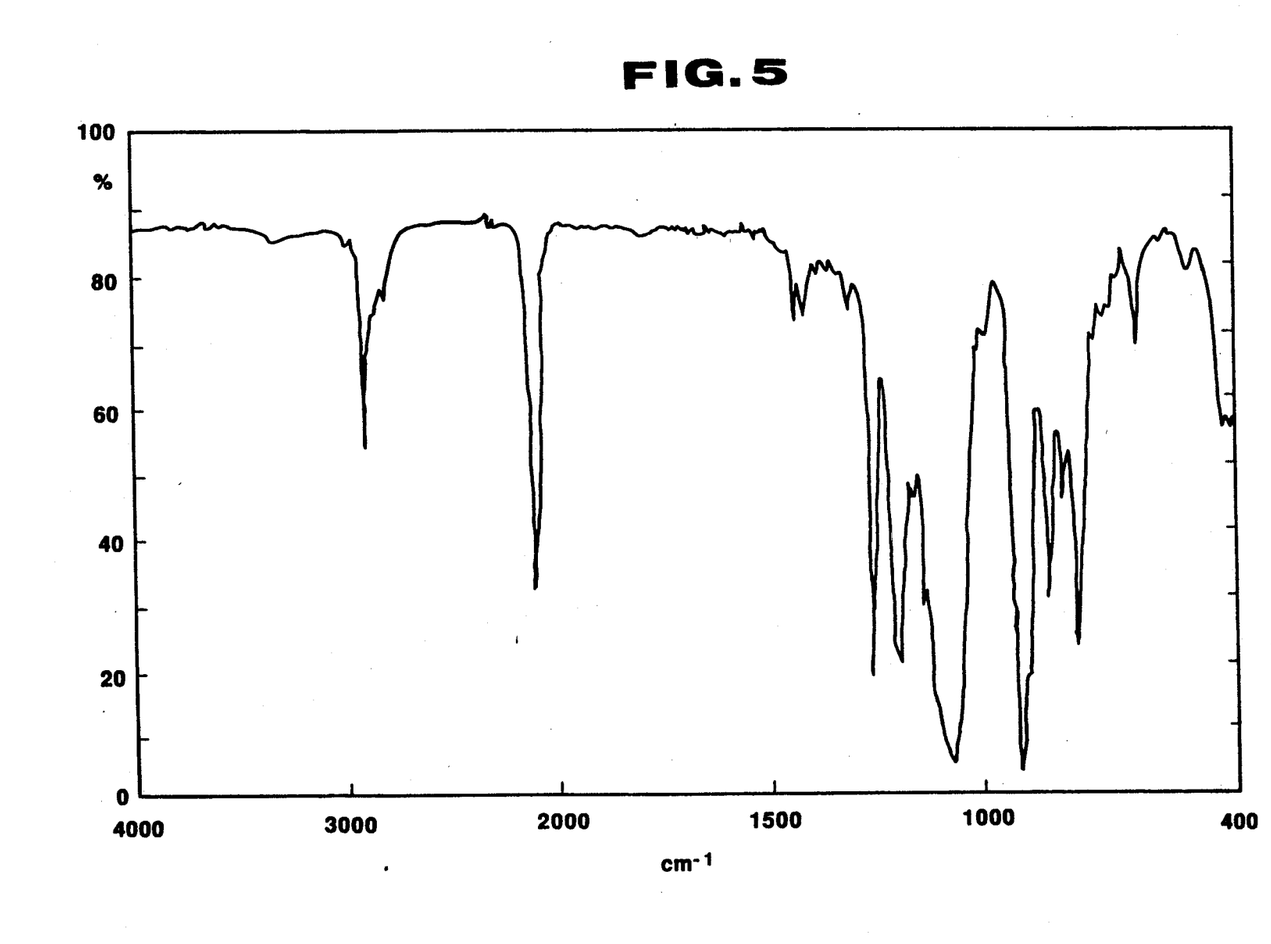

There appeared a characteristic absorption peak attributable to a SiH group at wavenumber 2140 cm$^{-1}$ and a characteristic absorption peak attributable to an epoxy group (C—H) at wavenumber 3000–3080 cm$^{-1}$. FIG. 5 is an IR absorption spectrum chart of the compound.

SiH content

Calcd.: 0.0051 mol/g
Found: 0.0048 mol/g

| $^1$H-NMR spectrum | |
|---|---|
| 4.53~4.87 ppm | (Si—H, m, 5H) |
| 0.07~0.40 ppm | (Si—CH$_3$, m, 36H) |
| 0.40~1.03 ppm | (Si—CH$_2$—, m, 6H) |
| 1.83~2.50 ppm | (C—CH$_2$—CF, m, 4H) |
| 1.47~1.80 ppm | (C—CH$_2$—C, m, 2H) |
| 3.20~3.57 ppm | (C—CH$_2$—O, m, 4H) |
| 2.77~3.67 ppm |  (CH——C, m, 1H) |
| 2.30~2.67 ppm |  (C——CH$_2$, m, 2H) |

Example 6

A reactor as used in Example 1 was charged with 20 grams (0.016 mol) of a hydrogensiloxane of formula (18) and 10 grams of toluene. In a similar manner as in Example 1, 1.0 gram of a toluene solution containing 0.016 grams of platinum catalyst (Pt: 1.6×10$^{-6}$ mol) was added dropwise to the reactor, and thereafter, 7.0 grams of a toluene solution containing 2.0 grams (0.016 mol) of an epoxy compound of formula (12) was added dropwise over 60 minutes.

(18)

(12)

By following the same procedure as in Example 1, there was obtained 21.2 grams of a product. The product was analyzed by GPC to find that it contained 12.9 grams of a mono-adduct (yield 60%). As a result of various analyses, the mono-adduct isolated and collected by GPC was identified to have the structure of formula (22).

(19)

| | Elemental analysis | | | |
|---|---|---|---|---|
| | C | H | Si | F |
| Calcd.* (%) | 31.99 | 4.62 | 16.62 | 33.74 |
| Found (%) | 31.76 | 4.83 | 16.09 | 34.53 |

Mass spectrometry 1350 (M+)

SiH content

Calcd.: 0.0037 mol/g
Found: 0.0034 mol/g

| $^1$H-NMR spectrum | |
|---|---|
| 4.53~4.90 ppm | (Si—H, m, 5H) |
| 0.03~0.43 ppm | (Si—CH$_3$, m, 36H) |
| 0.47~0.93 ppm | (Si—CH$_2$—C, m, 6H) |
| 1.87~2.53 ppm | (CF—CH$_2$—C, m, 4H) |
| 1.33~2.93 ppm | (C—CH$_2$—C, m, 8H) |
| 2.03~2.20 ppm | (C—CH—C, m, 1H) |
| 2.90~3.13 ppm |  (C——CH—, m, 2H) |

Example 7

A 200-ml three-necked flask equipped with a reflux condenser and thermometer was charged with 15 grams of toluene and 30.0 grams (0.025 mol) of a hydrogensiloxane of the following formula.

The flask was heated to a temperature of 70 to 80° C. With thorough stirring, 1.0 gram of a toluene solution containing 0.024 grams 2-ethylhexanol-modified complex of chloroplatinic acid catalyst having a platinum concentration of 2% (Pt: $2.5 \times 10^{-6}$ mol) was added dropwise to the flask. Thereafter, 8.8 grams of a toluene solution containing 3.8 grams (0.025 mol) of an alkoxy compound: $CH_2=CHSi(OCH_3)_3$ was added dropwise over 90 minutes.

The reaction mixture was allowed to cool down, shaken for 1 hour together with activated carbon, removed of the activated carbon by filtration, and subjected to vacuum distillation at 110° C. and 10 mmHg for 1 hour for solvent removal, obtaining 36.5 grams of a product. The product was analyzed by gel permeation chromatography (GPC) to find that it contained 20.1 grams of a mono-adduct (yield 59%).

The end compound was analyzed by proton-NMR, mass spectroscopy, IR absorption spectroscopy, elemental analysis and Si—H content measurement. As a result of these analyses, the mono-adduct isolated and collected by GPC was identified to have the structure of the following formula.

| | Elemental analysis | | | |
|---|---|---|---|---|
| | C | H | Si | F |
| Calcd.* (%) | 28.82 | 4.51 | 18.34 | 33.19 |
| Found (%) | 27.54 | 4.71 | 17.66 | 32.14 |

*calculated as $C_{33}H_{62}O_{13}F_{24}Si_9$

Mass spectrometry 1374 (M+)

IR absorption spectrum

Figure 6:
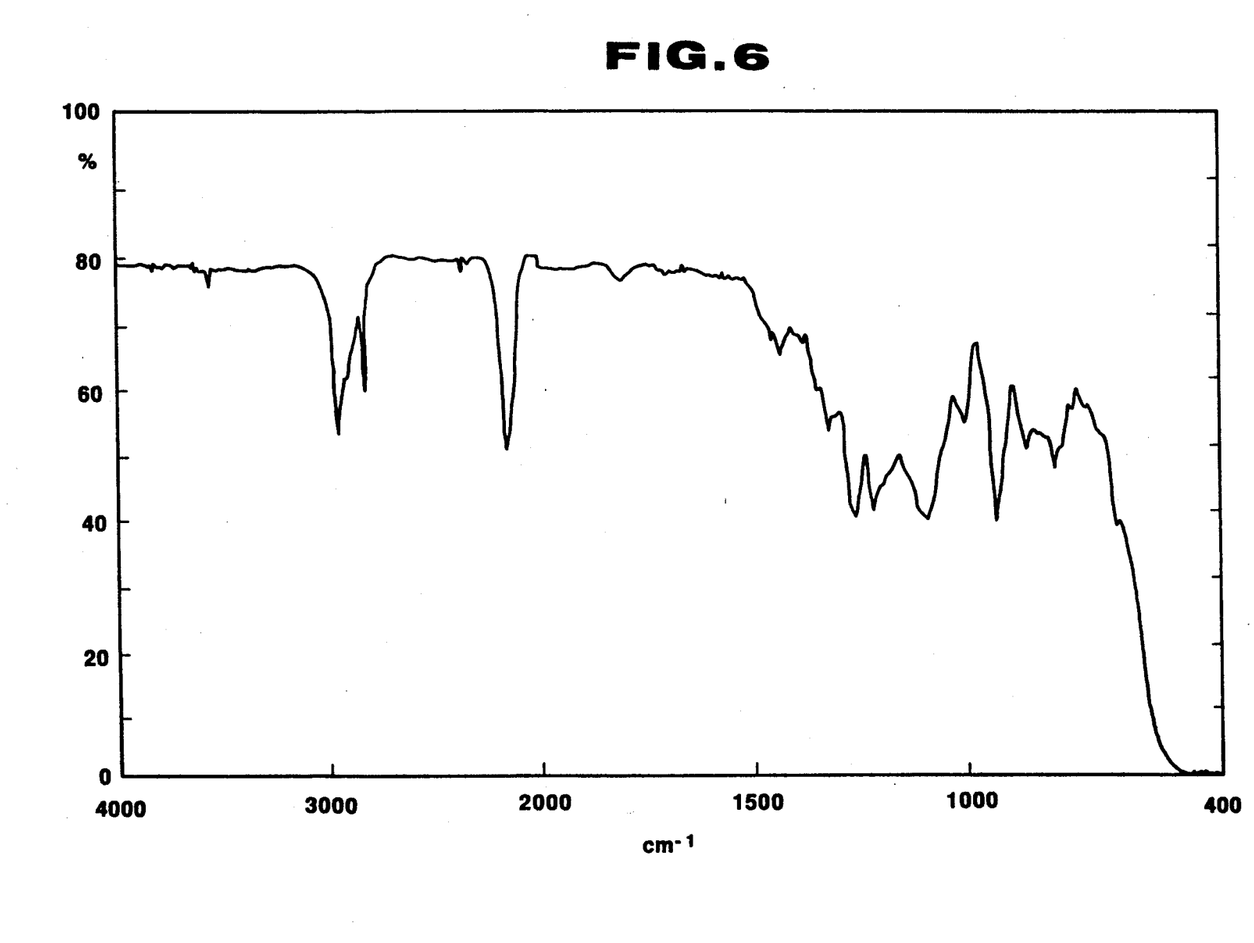

There appeared a characteristic absorption peak attributable to a SiH group at wavenumber 2140 cm$^{-1}$ and a characteristic absorption peak attributable to Si—OCH$_3$ at wavenumber 2850 cm$^{-1}$. FIG. 6 is an IR absorption spectrum chart of the compound.

SiH content

Calcd.: 0.0036 mol/g
Found: 0.0031 mol/g $^1$H-NMR spectrum: (solvent CDCl$_3$, internal standard TMS)

0.03~0.33 (Si—CH$_3$, 36H, m)
0.40~1.27 (Si—CH$_2$, 8H)
1.67~2.50 (C—CH$_2$—C, 4H)
3.13~3.73 (O—CH$_3$, 9H, m)
4.50~4.90 (Si—H, 5H, m)

BENEFITS OF THE INVENTION

There have been described novel siloxane compounds which are effective for imparting adhesion to a wide variety of resins. They are useful tackifiers for imparting adhesion to not only conventional resins, but also fluorinated silicone resins and rubbers since they have good affinity to fluorinated silicone resins and rubbers by virtue of the inclusion of a fluorinated group. They also make a great contribution to solvent resistance and reduced water permeability.

We claim:

1. A siloxane compound of the following formula (1):

wherein Rf is a perfluoropolyether group or perfluoroalkylene group, X is a group of the following formula (2), (3) or (4):

wherein R$^1$ is a divalent organic group, R$^2$ is a monovalent hydrocarbon group, and k is an integer of from 0 to 2, and letters n and m are integers of from 0 to 3 meeting $0 < n + m \leq 5$.

2. The siloxane compound of claim 1, wherein the Rf group is a perfluoropolyether having 4 to 15 carbon atoms and 2 to 5 oxygen atoms.

3. The siloxane compound of claim 1, wherein the Rf group is a perfluoroalkylene group having 2 to 10 carbon atoms.

4. The siloxane compound of claim 1, wherein the X group is of the formula (2).

5. The siloxane compound of claim 1, wherein the X group is of the formula (3).

6. The siloxane compound of claim 1, wherein the X group is of the formula (4).

7. The siloxane compound of claim 1, wherein one of n or m is the integer 0.

8. The siloxane compound of claim 1, wherein neither n nor m are the integer 0.

* * * * *